United States Patent [19]

Gombrich

[11] Patent Number: 4,916,441
[45] Date of Patent: Apr. 10, 1990

[54] PORTABLE HANDHELD TERMINAL

[75] Inventor: Peter P. Gombrich, Boulder, Colo.

[73] Assignee: CliniCom Incorporated, Boulder, Colo.

[21] Appl. No.: 246,520

[22] Filed: Sep. 19, 1988

[51] Int. Cl.<sup>4</sup> .................. H04Q 1/00; G06F 15/06
[52] U.S. Cl. ...................... 340/712; 341/22;
341/23; 340/825.300; 340/825.440; 364/709.11;
364/200; 235/380; 235/382; 235/462; 235/472;
455/89

[58] Field of Search ............... 235/380, 382, 385, 454,
235/462, 472; 364/705.1, 706, 707, 708, 709.01,
709.06, 709.11, 709.12, 413.02, 200 MS File,
900 MS File; 340/825.3, 825.31, 825.44, 712,
711, 706; 341/20, 22, 23; 178/18, 19; 455/89,
90, 95

[56] References Cited

U.S. PATENT DOCUMENTS

| D. 281,977 | 12/1985 | Sklaroff . | |
|---|---|---|---|
| 3,685,723 | 8/1972 | Berler . | |
| 3,826,900 | 7/1974 | Moellering . | |
| 3,971,925 | 7/1976 | Wenninger et al. | 341/26 |
| 4,006,397 | 2/1977 | Catotti et al. . | |
| 4,121,574 | 10/1978 | Lester . | |
| 4,143,417 | 3/1979 | Wald et al. | 340/711 |
| 4,180,204 | 12/1979 | Koenig et al. . | |
| 4,210,802 | 7/1980 | Sakai . | |
| 4,227,258 | 10/1980 | Root et al. . | |
| 4,251,798 | 2/1981 | Swartz et al. . | |
| 4,279,021 | 7/1981 | See et al. | 364/709.1 |
| 4,335,303 | 6/1982 | Call . | |
| 4,359,631 | 11/1982 | Lockwood et al. . | |
| 4,408,120 | 10/1983 | Hara et al. . | |
| 4,409,470 | 10/1983 | Shepard et al. . | |
| 4,411,016 | 10/1983 | Wakeland . | |
| 4,456,793 | 6/1984 | Baker et al. . | |
| 4,460,120 | 7/1984 | Shepard et al. . | |
| 4,471,165 | 9/1984 | DeFino et al. . | |
| 4,471,345 | 9/1984 | Barrett, Jr. . | |
| 4,481,382 | 11/1984 | Villa-Real . | |
| 4,483,683 | 11/1984 | Alley, Sr. . | |
| 4,486,624 | 12/1984 | Puhl et al. . | |
| 4,488,035 | 12/1984 | Withnall et al. . | |
| 4,488,678 | 12/1984 | Hara et al. . | |
| 4,489,313 | 12/1984 | Pfister . | |
| 4,491,725 | 1/1985 | Pritchard . | |
| 4,496,831 | 1/1985 | Swartz et al. . | |
| 4,503,288 | 3/1985 | Kessler . | |
| 4,508,935 | 4/1985 | Mastromoro . | |
| 4,519,066 | 5/1985 | Barrett, Jr. et al. . | |
| 4,523,087 | 6/1985 | Benton . | |
| 4,528,443 | 7/1985 | Smith . | |
| 4,528,444 | 7/1985 | Hara et al. . | |
| 4,569,421 | 2/1986 | Sandstedt . | |
| 4,570,057 | 2/1986 | Chadima, Jr. et al. . | |
| 4,575,625 | 3/1986 | Knowles . | |
| 4,578,571 | 3/1986 | Williams . | |
| 4,588,881 | 5/1986 | Pejas et al. . | |
| 4,593,155 | 6/1986 | Hawkins . | |
| 4,621,189 | 11/1986 | Kumar et al. . | |
| 4,625,276 | 11/1986 | Benton et al. . | |
| 4,628,193 | 12/1986 | Blum . | |
| 4,634,810 | 1/1987 | Grassl et al. . | |
| 4,654,818 | 3/1987 | Wetterau, Jr. | 364/709.12 |
| 4,680,455 | 7/1987 | Kuo | 364/709.1 |
| 4,692,740 | 9/1987 | Washizuka et al. | 341/22 |
| 4,739,316 | 4/1988 | Yamaguchi et al. | 340/711 |
| 4,773,032 | 9/1988 | Uehara et al. | 364/709.12 |
| 4,806,906 | 2/1989 | Oda et al. | 364/709.12 |
| 4,835,372 | 5/1989 | Gombrich et al. | 235/462 |

OTHER PUBLICATIONS

"Potential use of bar codes to implement automated dispensing quality assurance programs," *Hospital Pharmacy*, vol. 20, May 1985, by Hokanson et al., pp. 327-329, 333 & 337, Exhibit A.

(List continued on next page.)

Primary Examiner—Donald J. Yusko
Assistant Examiner—E. O. Pudpud
Attorney, Agent, or Firm—Merchant, Gould, Smith, Edell, Welter & Schmidt

[57] ABSTRACT

A handheld pocket terminal (22) having a display screen (40) and a bar code reader (42).

13 Claims, 9 Drawing Sheets

OTHER PUBLICATIONS

"Bar Coding for Medical Device Labeling," *MD&DI*, Aug. 1983, by Richard Farb, pp. 27-29 & 88, Exhibit B.

"A uniform labeling system for blood services" by Hubbell et al., *Medical Instrumentation*, vol. 15, No. 1, Jan.-Feb. 1981, pp. 61-63, Exhibit C.

"Bar code finds identity as user-input alternative," *Systems and Software*, Apr. 1985, by Ron Schneiderman, Exhibit D.

"An integrated hospital computer system," *Systems Technology*, Dec. 1978, No. 30, Stobart et al., Exhibit E.

"The Databar Scan: OSCAR makes it easier for computer users to get with the program," Corporate Report, Apr. 1984, by Pamela Espeland, Exhibit F.

Product Announcement, Databar DBR 1000, Modular Bar Code Scanner System, Copyright 1984, Databar Corporation, Eden Prairie, Minn., Exhibit G.

Databar DBR 1000, Bar Code Scanners, Copyright 1984, Databar Corporation, Eden Prairie, Minn., Exhibit H.

Handout entitled, "Cost Benefit Analysis of the Clinicare Handheld Terminal System", presented by Shirley Hughes, R.N., at the 1987 Healthcare Systems Conference, Feb. 9-13, 1987, pp. 1-21, (Exhibit C).

Article entitled, "Travenol Laboratories: A Leader in HIBC", *Bar Code News*, Sep./Oct., 1986, pp. 40-45, (Exhibit F).

One-page article entitled, "CliniCom . . . Something New on the Horizon", *HC&C*, Oct., 1986, p. 16, (Exhibit G).

One-page article entitled, "Patient-Centered Clinical Information System", published Oct., 1986, (Exhibit I).

Article entitled, "Qualitative & Quantitative Benefits of the Clinicare Bedside System by CliniCom, Incorporated", Feb., 1987, pp. 1-12, (Exhibit O).

Successfully Implementing a Point-of-Care System", by Mary Yero, *Computers in Healthcare*, Feb. 1988, pp. 24-25, (Exhibit A/4-5-89).

"Bedside Data Systems Aids Pharmacy", by Karen Gammon, R.P.H., and Kristi Robinson, R.P.H., *Computers in Healthcare*, Dec. 1988, pp. 35-37, (Exhibit B/4-5-89).

"St. Francis Hospital Goes Bedside and Beyond", by Mary Yero, *HC&C*, Jan. 1988, pp. 48, 50 & 52, (Exhibit C/4-5-89).

*Bedside Terminals: CliniCom*", by Shirley Hughes, *M. D. Computing*, vol. 5, No. 1, 1988, pp. 3 & 22-28, (Exhibit D/4-5-89).

"Firm's product aids medical personnel", by Julie Truck, *Daily Camera/Business Plus*, Nov. 24, 1987, p. 3, (Exhibit E/4-5-89).

"Dustbuster-size scanner tracks drug dispensing", by Mark Talge, *The Denver Post*, Apr. 11, 1988, (Exhibit F/4-5-89).

"CliniCom to install information system", *Daily Camera/Business Plus*, Oct. 18, 1988, (Exhibit G/4-5-89).

"CliniCom's Electronic Charting Takes High-Tech to Hospital Beside", by Nancy Nachman-Hunt, *Boulder County Business Report*, Oct. 1988, (Exhibit H/4-5-89).

"As the Industry Matures . . . ", *Computers in Healthcare*, Nov. 1988, (Exhibit I/4-5-89).

"Being a miracle worker with only two hands is not as impossible as it sometimes seems", one—page, CliniCom, Inc., brochure, (Exhibit J/4-5-89).

"Bedside computer tested in Topeka", by Vickie Griffith Hawver, *The Topeka Capital Journal*, Jan. 16, 1988, two-page article, (Exhibit K/4-5-89).

"CliniCom Consumable Supplies-Pricing and Ordering Information Sheet", CliniCom Incorporated, Oct. 1988, (Exhibit L/4-5-89).

"Point of Care Terminal—Product Information Sheet", CliniCom Incorporated, Dec. 5, 1988, (Exhibit M/4-5-89).

"Cliniview—Product Information Sheet", CliniCom Incorporated, Jan. 25, 1989, (Exhibit N/4-5-89).

"Cliniview with Touchscreen", CliniCom Incorporated, (Exhibit O/4-5-89).

"Unicode-Product Information Sheet", CliniCom Incorporated, Jun. 16, 1988, (Exhibit P/4-5-89).

"MPI Bulk Medication Packager: Hardware, Software, and Consumables-Pricing and Ordering Information Sheet", CliniCom Incorporated, Mar. 16, 1988, (Exhibit Q/4-5-89).

"CliniCom: Barcode Support Items-Pricing and Ordering Information Sheet", CliniCom Incorporated, Jun. 16, 1988, (Exhibit R/4-5-89).

"Unicode TM Printer-Product Information Sheet", CliniCom Incorporated, Mar. 18, 1988, (Exhibit S/4-5-89).

"Terminal Support Unit (TSU)-Product Information Sheet", CliniCom Incorporated, Jun. 16, 1988, (Exhibit T/4-5-89).

"St. Francis Hospital and Medical Center to Add High Touch Technology", press release, CliniCom Incorporated, Jun. 3, 1987, (Exhibit U/4-5-89).

OTHER PUBLICATIONS

"CliniCom Incorporated Announces Venture Capital Funding", press release, CliniCom Incorporated, Dec. 23, 1987, (Exhibit V/4–5–89).

"CliniCom Incorporated Finalized Second Round of Venture Capital Funding", press release, CliniCom Incorporated, Feb. 24, 1988, (Exhibit W/4–5–89).

"CliniCom Incorporated Announces Management Changes", press release, CliniCom Incorporated, May 26, 1988, (Exhibit X/4–5–89).

"Children's Hospital of Orange County Chooses CliniCom's Point of Care Clinical Information System", press release, CliniCom Incorporated, Oct. 3, 1988, (Exhibit Y/4–5–89).

"CliniCom Offers Productivity Improvement Program", press release, CliniCom Incorporated, Feb. 24, 1989, (Exhibit Z/4–5–89).

"Point–Of–Care: Being a Pilot Site", by Bill W. Childs, *U.S. Healthcare*, pp. 23–24, reprinted Dec. 1988, (Exhibit AA/4–5–89).

"The Bedside Story", CliniCom Incorporated newsletter, vol. 2, No. 1, Spring/Summer 1988, (Exhibit BB/4–5–89).

"Beside matters–CliniCare TM . . . A cost control, productivity, risk management system", six-page CliniCom brochure, ©1989, (Exhibit CC/4–5–89).

"A Summary of the Benefit Results of the Clinicare Bedside System at St. Francis Hospital", seven—page report by CliniCom, (Exhibit DD/4–5–89).

"Prescription for Profits", by Patrick Houston, *Success*, Apr. 1989, p. 29, (Exhibit EE/4–5–89).

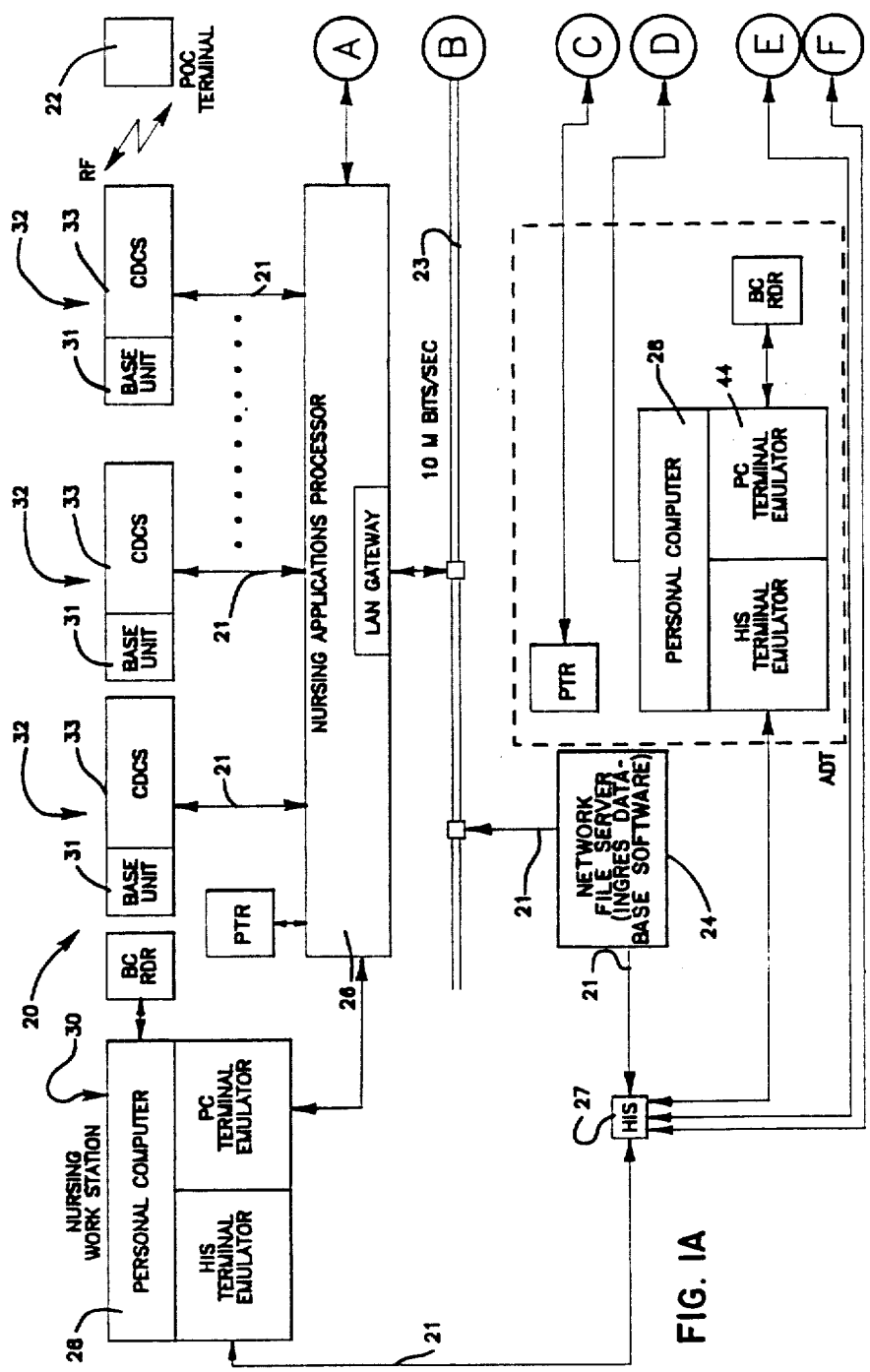
FIG. IA

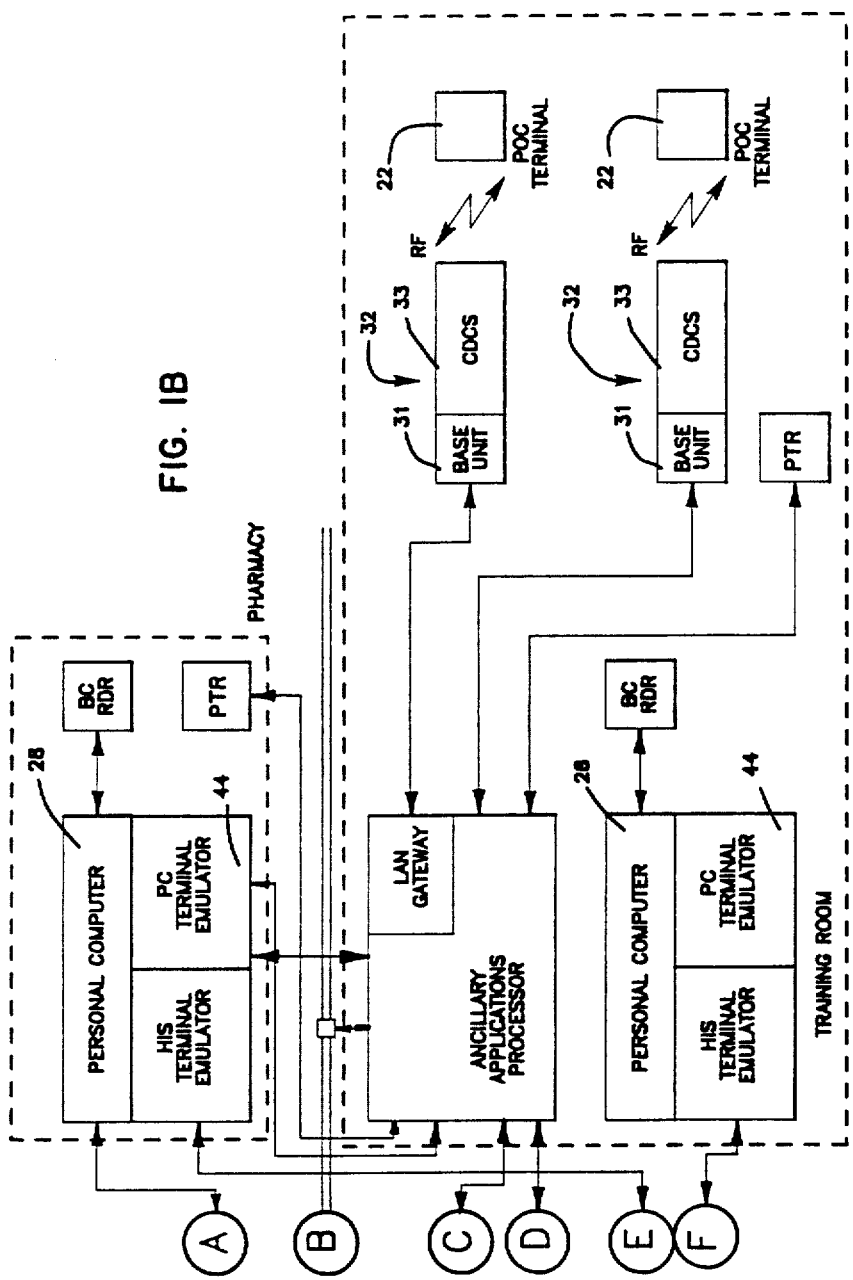

PORTABLE HANDHELD TERMINAL

BACKGROUND OF THE INVENTION

The present invention relates to a portable handheld terminal and in particular a point of care portable handheld terminal utilized in a patient care system.

Medical institutions are faced with a competitive environment in which they must improve profitability and yet simultaneously improve patient care. There are several factors which contribute to the ever increasing cost of hospital care. For example, there is an ever increasing amount of paperwork required by nuses, physicians, pharmacists, and laboratory personnel. In addition, inaccurate recording of patient care provided, drugs, supplies, and tests involved in patient care results in poorer quality of care and in decreasing revenues by failure to fully capture billing opportunities of these actual costs. Inadequate management also results in a failure to provide an accurate report of all costs involved in treating a particular illness.

Moreover, the lack of accurate and rapid transfer of patient information often reduces the accuracy and/or effectiveness of drug administration and patient care, thereby increasing the duration of hospital stay.

In addition, as health care facilities continue to decrease the number of staff personnel as a cost cutting measure and due to the shortage of qualified personnel in the health care field, the possibility of errors in patient care will probably increase.

Further, reductions of the number of staff personnel and increasing automation of patient monitoring systems may result in less time spent by a staff person at each patient's bedside, thus exacerbating psychological stressors on the patient and negatively affecting patient care.

Applicant has filed commonly assigned applications having U.S. Pat. Nos. 4,814,759, 4,835,372, and 4,850,009, which relate to health care systems and which are hereby incorporated by reference.

The present invention offers a system which solves or at least reduces the impact of the above-identified problems and other difficulties associated with health care facilities.

SUMMARY OF THE INVENTION

The present invention relates to a portable handheld terminal and in particular a portable handheld terminal utilized in a point of care patient care system.

Applications offered by the present invention utilize a handheld unit and, as such, deal with functions routinely performed at the patient location such as at bedside, in the patient's home, in the hallways, etc., where limited amounts of information are required at any given time.

An object of the current invention is to provide a portable terminal for data input, since a stationary terminal has been determined to be restrictive in the course of providing patient care.

Another object of the current invention is to provide a full screen monitor which allows for fast and accurate data entry methods, and minimizes the time required to request data and the time spent in documentation.

Yet another object of the current invention is to provide a system having additional automated bedside applications supporting documentation of observations as narrative notes, recording patient care and outcome observations such as care planning assessments and routine care, and retrieval of test results, physician orders, and other large quantities of patient data.

Still another object of the current invention is to provide a system for fast, accurate, and portable data input capability for health care professionals, designed around menu selection and/or bar code data entry using a handheld point of care terminal as the "keyboard", touch selection methodology, and/or bar code reader. This approach minimizes free text keyboard type data entry requirements. Usefulness is not compromised as it is estimated that less than 10 percent of all documentation will require any free text entry. In most cases, the types of data requiring free text keyboard entry will be summary statements and/or subjective observations about the patient's progress. These types of entries can typically be done once per shift at a nursing station terminal or by using the bedside full screen monitor touch screen alpha-numeric character selection to type in additional information.

Still another object of the current invention is to provide a system which offers the flexibility to allow a nurse the capability to document either at bedside or at a nursing station terminal, thus allowing the nurse to control the patient environment. For example, it may be appropriate to document what has been accomplished on a patient as care is provided at bedside, while more extensive notes and observations of progress are documented at a nursing station terminal so as to not disturb the patient's privacy.

Yet another object of the current invention is the incorporation of features and capabilities of the current invention into an IBM personal computer or compatible terminal which can then be used by both the patient care system and existing hospital information system at the nursing station.

Still another object of the current invention is to provide for the customization of menu selections, wherein a hospital may build or modify the screen content.

Still another object of the current invention is to provide retrieving and display of a single patient's clinical information in the patient's room on a clinical care monitor station. Data available for display includes any stored in the patient care system data base which has been entered into the patient care system and data such as test results sent from the hospital information system to the patient care system for storage.

Yet another object of the current invention is to provide display of numerical information retrieved on the patient care system in graphic format. A graphic capability is especially helpful in illustrating trends in vitals signs and lab results.

Still another object of the current invention is providing storage of all active M.D. orders for retrieval and statusing. Once the orders are displayed, a status flag of DISCONTINUED, RENEW or HOLD may be input into the patient care system and passed back to the hospital information system.

Still another object of the current invention is to provide documentation of care given, assessment of the patient condition and progress toward care planning goals.

Yet another object of the current invention is to provide a full care planning capability for development and implementation of patient care plans.

Still another object of the current invention is to provide retrieval of critical patient information with an emergency access code and display of this information for use by an emergency care team.

Yet another object of the current invention is to provide a personal order set capability for physician order entry. This allows each physician to define the orders he or she most prescribes to be accessed via the patient care system at the bedside and activated for a given patient.

Still another object of the current invention is to minimize the number of terminals required for the hospital, thus reducing system cost.

Yet another object of the current invention is to minimize the space required in a patient room.

Still another object of the current invention is to increase the speed of communication and thus decrease end user response time through an improved communications network.

Yet another object of the current invention is to increase applications processing and information availability through distribution of processing functions.

Yet another object of the current invention is to provide greater data accessibility to the health care giver.

Still another object of the current invention is to minimize the number of times a sign-on process is repeated while maximizing security in the patient care system.

Yet another object of the current invention is to improve reminder functions of the patient care system to prevent omissions of prescribed care.

Still another object of the current invention is to increase ease of data entry with the addition of flexible touch keypad capability in the patient care system.

Yet another object of the current invention is to provide physicians with access to their patient's data to enter and/or change orders from remote locations.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views:

FIGS. 1A,1B are a system diagram of an embodiment of a patient care system communicating information through a local area network (LAN) in accordance with principles of the present invention;

DETAILED DESCRIPTION OF THE PREFERRED EMBODIMENT

Figure 2:
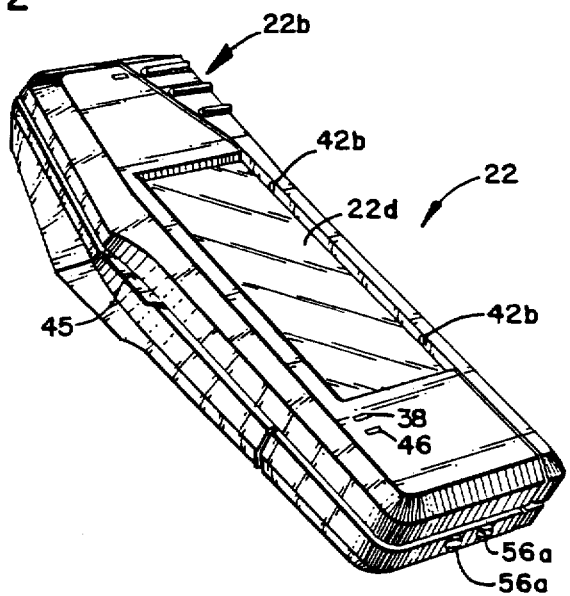
FIG. 2 is a perspective view of a embodiment of a portable handheld terminal in accordance with the principles of the present invention, also referenced as a point of care terminal.

While the detailed description is provided in terms of a hospital environment, it will be appreciated that the present invention has application and utility to a variety of patient care facilities such as home health care and nursing homes, wherein patient identification and relating items including such disposable items as drugs or supplies to a particular patient is desirable and important for proper care, administration, inventory control, and billing.

Referring now to the drawings, there is illustrated in FIG. 1 an embodiment of a patient care system, generally referred to by the reference number 20 utilizing a pocket terminal 22 in accordance with the principles of the present invention. The pocket terminal 22 is also referred to as a point of care (POC) terminal since it can be used by the health care professional where the care is being administered. As illustrated, the patient care information system 20 is a high speed and reliable distributed processing and communications LAN network using the pocket-sized, battery-powered portable terminal 22 as the point of care data input and retrieval device.

The communications environment is based on a high speed local area network which uses existing telephone wiring 21 in patient rooms or, optionally, dedicated twisted pair wires, linked to a central backbone cable 23; e.g., ethernet, which is, in turn, linked to a central file server system 24 including a computer and support peripheral devices such as disk drives for storing large amounts of information. It will be appreciated that other types of cabling such as coax and fiber optic might also be used. A nursing applications processor 26, along with other such processors (not shown), acts as the focal point for processing patient care information in a distributed manner. The nursing application processor 26 will include most of the application software and related data. Examples of such application functions might include charting, note taking, planning, administration, vital signs, etc. The file server 24 will include a centralized patient data base and associated software.

The patient data base will be updated as required due to admitting, discharge, transfer, miscellaneous application functions, etc. carried out at the various terminals in the patient care facility. While the centralized patient care data base is contained at the file server 24, selected patient data can be updated at the applications processor 26 and then transferred to the file server 24. For example, when working with a patient, the data for that patient might be transferred to the appropriate applications processor 26 and updated at the applications processor 26 before being transferred back to the server 24. In the preferred embodiment, to enable integration with any existing hospital information system (HIS) 27 which might co-exist with the patient care system, a high speed, high transaction load personal computer 28 is used at a nursing station 30 including PC terminal emulator functions for interfacing with the nursing applications processor 26 of the patient care system 20; e.g., data input and retrieval functions, and including HIS terminal emulator functions for input and retrieval of data from the HIS system. The computer 28 might be, for example, an IBM RT/PC, Model 135. If the nursing station 30 is only used to interface with the patient care system 20, then a much less powerful computer can be used such as one using an Intel 8088 processor. In addition, the centralized file server 24 is also interconnected to the HIS system 27 so as to allow interfacing of the patient care system with the HIS system 27 whereby data can be exchanged with the patient care system. The centralized file server 24 data base ensures data reliability and integrity while the local area network supports data accessibility to the end user within seconds.

Figure 5:
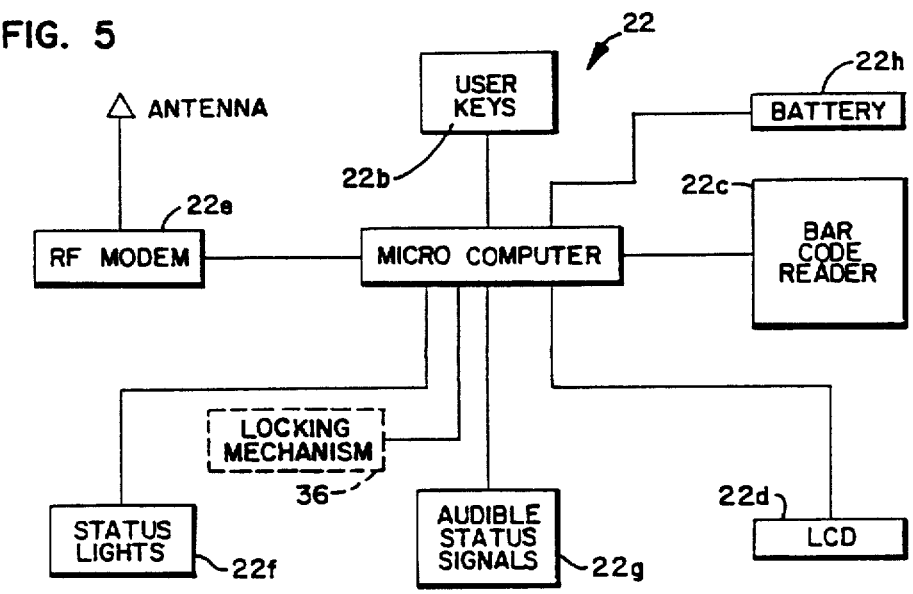
FIG. 5 is a block diagram of the portable handheld terminal.

FIG. 5 is a block diagram of various components of one embodiment of the pocket terminal 22. As illustrated, the pocket terminal 22 will typically include a microcomputer 22a for controlling the overall operation of the pocket terminal 22, user keys 22b for entering commands such as transmit information, a bar code reader 22c for reading bar code indicia, a programmable liquid crystal display (LCD) 22d which is utilized as a keypad for entry of data by the user and for display of information, a wireless transmitter such as an RF modem, also referred to as an RF transceiver, 22e for wireless transmission of information (other wireless transmitters such as infrared transmitters might be used), status lights 22f for indicating miscellaneous status of the system, audible status signals 22g for providing an audible status signal to the end user, and batteries 22h for powering the pocket terminal 22.

The portable pocket terminal 22 resides, when not in use, in a base unit 31 at the nursing station 30 (or any centrally located area), or in a wall mounted base unit 31 in the patient room. The base 31 includes suitable recharging circuitry which serves to recharge the pocket terminal batteries when the terminal 22 is at rest in the base unit 31. The pocket terminal includes electrically conducting contents 40 which engage similar contents on the inside of the base unit 31. The base unit 31, in turn, includes an electrical plug arrangement for interconnection with an AC outlet or other suitable power supply. The base unit 31 includes a suitable locking mechanism 36 which locks the pocket terminal 22 in the base unit 31 such that the pocket terminal 22 is only released for use by authorized users.

Figure 13:
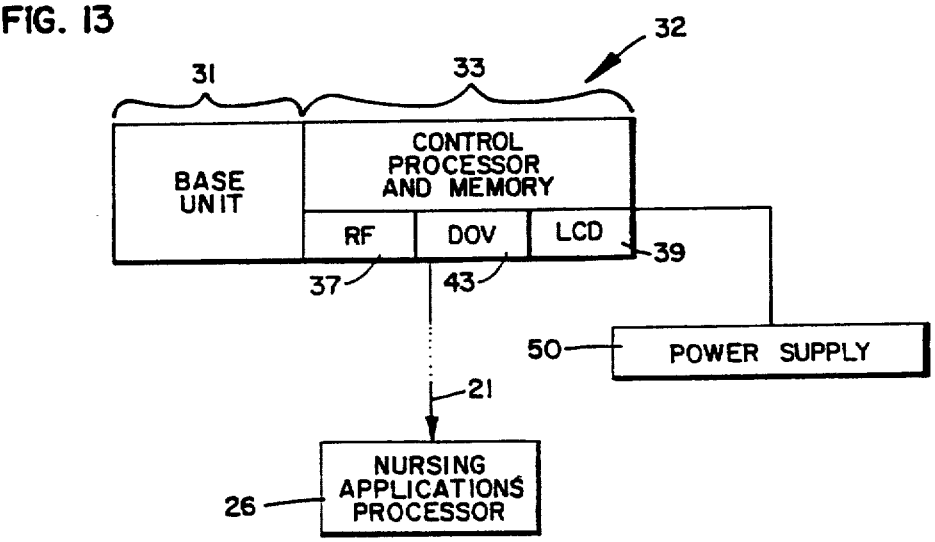
FIG. 13 is a block diagram of an embodiment of a base station in accordance with the principles of the present invention.

As discussed, the pocket terminal 22 may be used with a wall-mounted base unit 31 in the patient room rather than at the nursing station 30. This option may be installed throughout the hospital or may be selected as the method of choice only in certain areas of the facility. With the base unit 31 in the patient room, the hospital may choose to configure the system to simply verify the user sign-on and then release the base station lock without downloading information to the pocket terminal 22. The hospital may configure which base units 31 can be used for downloading of information; e.g., from the patient care data base and which are simply used as pocket terminal recharger base units. When used simply for recharging purposes, the base unit 31 need not be interconnected to the patient care data base. When used for downloading of information, the base unit 31 will be electrically interconnected via a suitable communications port to the personal computer at the nursing station 30 or to a clinical display communication station (CDCS) 33, as illustrated in FIG. 13. The nursing station 30 or clinical display communication station 33 will in turn be suitably interconnected to the patient care data base by suitable electrical conductors such as twisted pair wire 21. Together, the base unit 31 and the stations 30 or 33 will function as a base station (BS) 32.

Figure 3:
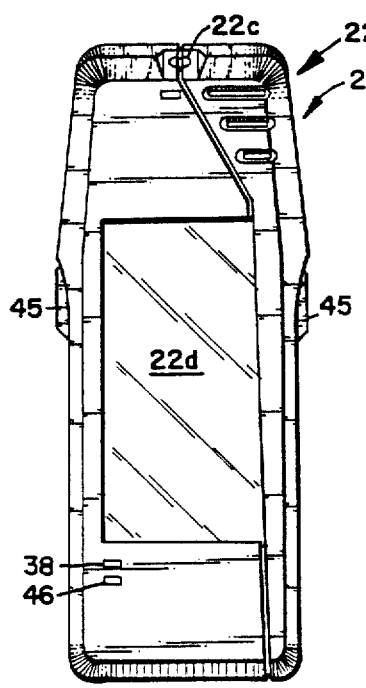
FIG. 3 is a front elevational view of the portable handheld terminal, showing a bar code scanner.
Figure 4:
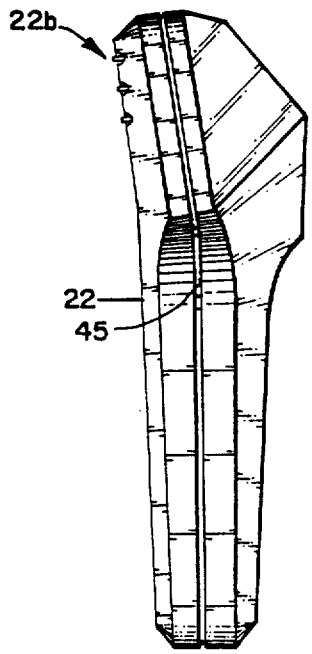
FIG. 4 is a right side view of the handheld terminal of FIGS. 2 and 3.
Figure 6:
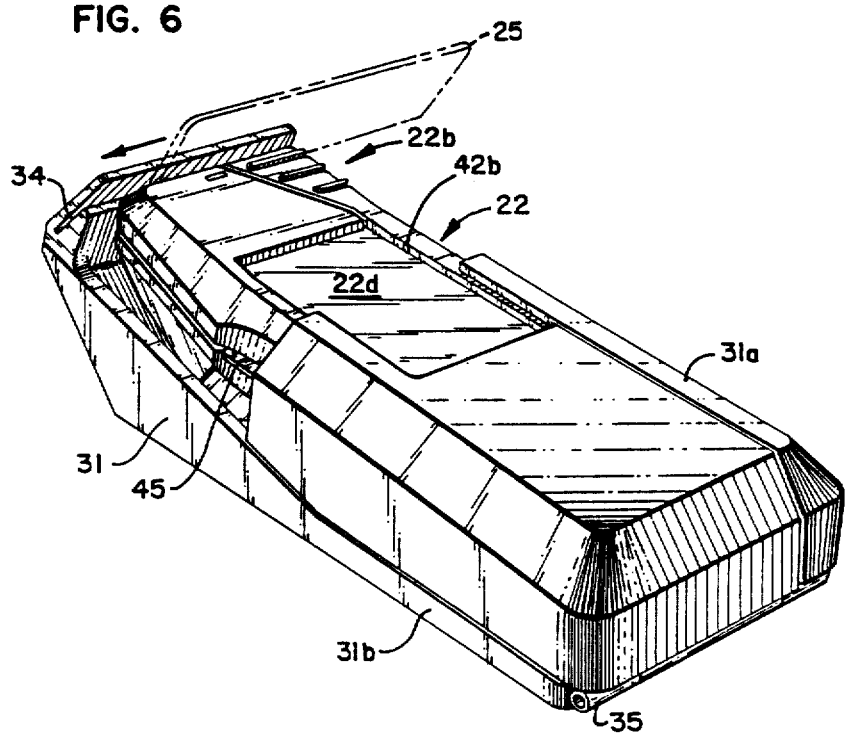
FIG. 6 is a perspective view of a portable handheld terminal in a holder therefor and having an identification card disposed in a slot of the terminal holder.
Figure 7:
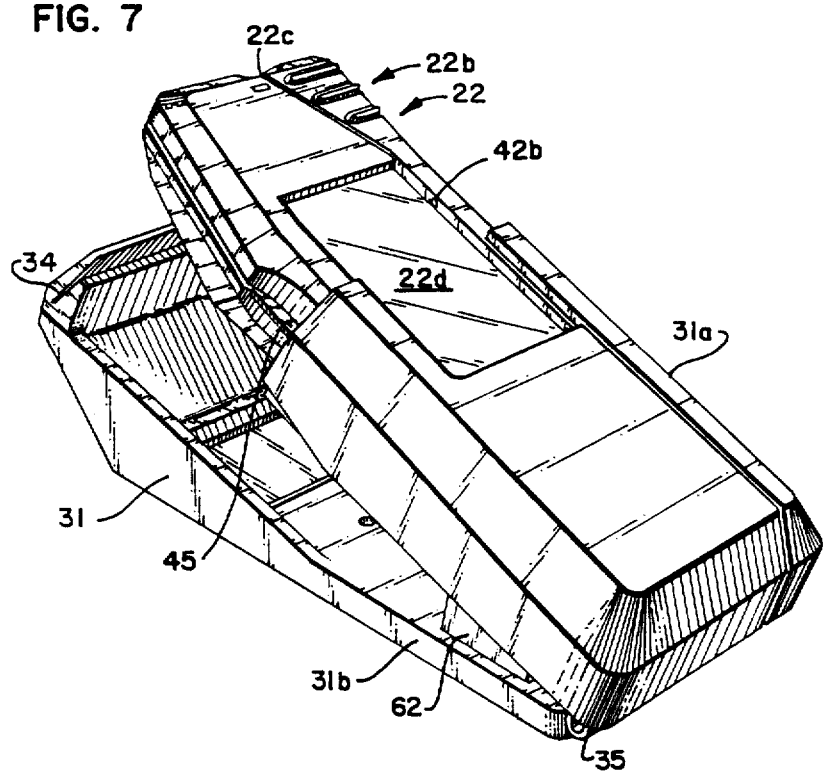
FIG. 7 is a perspective view of the portable terminal and the holder of FIG. 6 in an open position.
Figure 10:
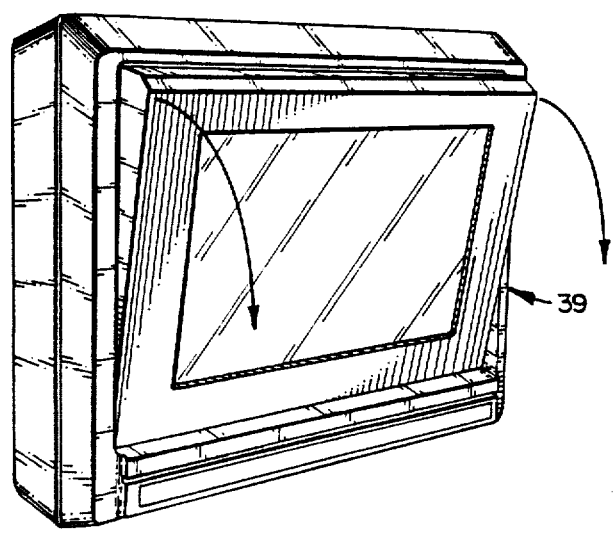
FIG. 10 is a front perspective view of an embodiment of a liquid crystal display monitor in accordance with the principles of the present invention.

When the user wishes to use the patient care 20 system, he/she signs into the pocket terminal 22 by first inserting a card 25 into a slot 34 in the base unit 31, as shown in FIG. 6, and turning on the bar code reader 22c by pressing the activation buttons 45 shown in FIG. 3. The card 25 includes bar code indicia representing user/patient identifier information, which indicia is read by the bar code reader 22. The user identifier information is then sent from the pocket terminal 22 to the patient data base at the file server 24 via the local area network which will include a verification program for verifying the user identifier information by comparing it against a data table of valid user identifiers. If the user identifier is valid, a signal will be sent from the file server to the base unit causing the locking mechanism to release whereby the pocket terminal can be removed. The verification program and the user identifier data table might also be located at the nursing applications processor 26 or at the clinical display communications station 33. Once the user identifier information has been verified, the locking mechanism unlocks the base unit 31 so that the pocket terminal 22 is released from the base unit 31 as generally illustrated in page 7 by pivotal movement of a base unit housing portion 31a relative to a base unit portion 31b about a clam shell arm release 35. The pocket terminal 22 is locked in the base unit 31 until this sign-on process is completed. Once sign-on is completed, the pocket terminal 22 may be removed by the user and is carried on his/her person while making rounds and caring for patients. However, before giving access to the patient care system, the user must enter his/her user identifier via use of the touch sensitive display 22d. Prompts on the pocket terminal liquid crystal display 22d instruct the user to type in user identifier information via the liquid crystal display 22d once the terminal 22 has been removed from the base unit 31. This information is once again sent via the high speed communications local area network to validate the user identifier information, and then to upload data specific to that user and his/her patient assignments, from patient care data base at the central file server 24 to the pocket terminal 22, if the user identifier information is found to be a valid user identifier. The user is notified that the unit is ready for use by means of a ready light 38 which is one of the status lights 22f on the pocket terminal 22.

Figure 14:
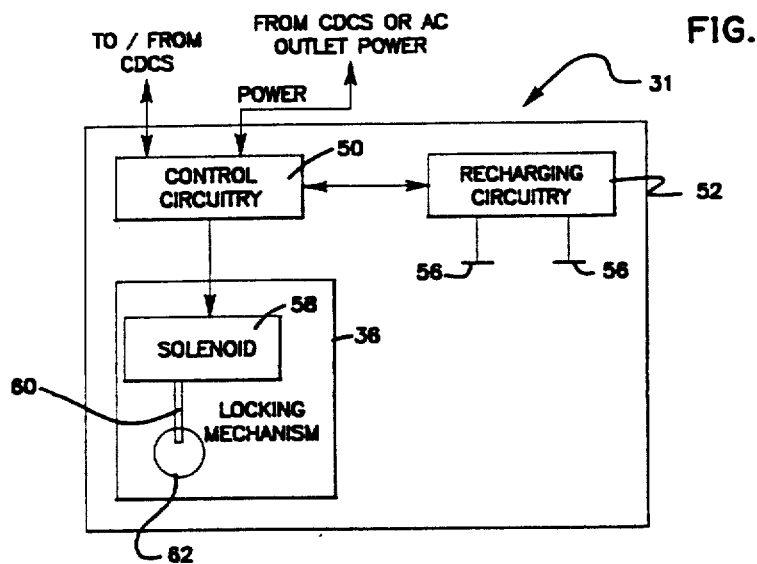
FIG. 14 is a block diagram of an embodiment of a base unit.
Figure 15:
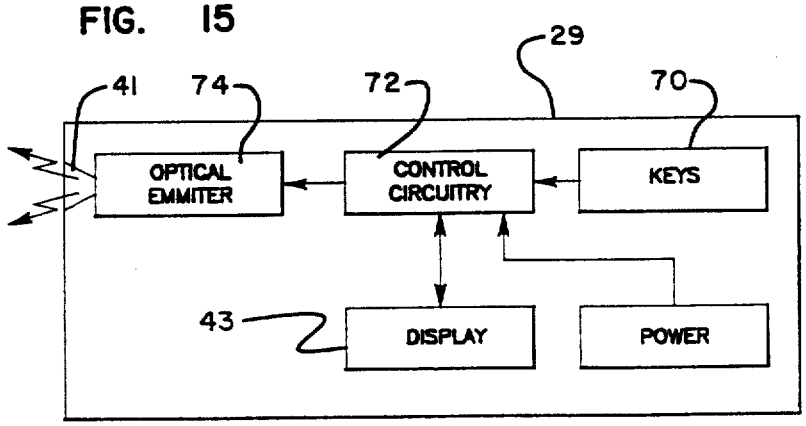
FIG. 15 is a block diagram of an embodiment of a detachable keypad.

FIG. 14 is a block diagram of an embodiment of the base unit 31 including control circuitry 50, recharging circuitry 52 for recharging the battery 22h of the pocket terminal 22, and locking mechanism 36. As illustrated, the recharging circuitry 52 includes suitable contacts 56 which are exposed so as to engage corresponding contacts on the pocket terminal 22 when the pocket terminal 22 is inserted into the base unit 31 so as to enable electrical contact to the battery 22h of the pocket terminal and thus recharging thereof. The locking mechanism 36 includes a solenoid 58 operating a locking pin 60 so as to engage an aperture or the like in a cam 62 when the base unit 31 is locked. The cam 62 in turn cooperates with the first and second 31a,b base unit housing portions so as to prevent pivotal movement thereof when the cam 62 is locked in place by the pin member 60. Upon withdrawal of the pin member 60 from the cam 62, the base unit first and second housing portions 31a,b are allowed to pivot relative to one another. Operation of the solenoid 58 is controlled by the control circuitry 50. The control circuitry 50, will in turn, activate the solenoid so as to unlock the base unit 31 upon receipt of an appropriate signal from the clinical display communications station (CDCS) 33. This signal will be sent to the control circuitry 50 of the base unit 31 if the user identifier scanned on the card 25 is found to be a valid user identifier. In turn, the control circuitry 50 is shown as receiving its power from the clinical display communications station 33 or an AC outlet. The locking mechanism 36 is structured such that when the base unit is closed, the locking pin 60 will engage the cam 62 and thus lock the base unit. It will be appreciated that a number of different locking mechanisms might be utilized and still be in keeping with the spirit of the present invention. In the preferred embodiment, the control circuitry 50 of the base unit 31 will monitor the recharging circuitry 52 so as to control the recharging process of the pocket terminal. The recharging circuitry 52 might also be used to recharge removable battery packs which might be suitably electrically connected to the recharging circuitry via another set of electrical contacts.

After a period of several minutes of inactivity on the terminal 22, it will be necessary for the user to re-enter a user identifier before entering or retrieving patient information. In the preferred embodiment, the period of inactivity allowed is adjustable. This prevents access into the patient care system 20 by unauthorized users who may find a pocket terminal 22 unattended.

When the base unit 31 is configured only as a patient terminal recharger, once the user sign-on is validated, the user may take the terminal 22 out of the base unit 31 and use the pocket terminal 22 for data input or retrieval by reading the patient bar codes. When the user is finished with the session, the pocket terminal 22 is replaced in the base unit 31 and is automatically signed off. As discussed, if the pocket terminal 22 remains out of the base unit 31 recharger for an extended period, the user may be required to re-enter his/her personal user identifier (ID) after several minutes of inactivity, but will not be required to reread the user bar code unless the pocket terminal 22 is replaced in the base unit 31. This will maintain user security while minimizing inconvenience to the user. This simple sign-on option without downloading may be desired in areas such as intensive care where a nurse typically cares for only one or two patients and remains at the patient bedside most of the time. The need for a portable data base is minimized in this environment since the base unit 31 can be easily accessed at all times.

The light weight (in one embodiment, approximately 16 ounces with approximate dimension of $3 \times 5 \times 1.5$ inches) pocket terminal 22 is made up of a transceiver (in one embodiment 900 mHz direct sequence frequency hopping, spread spectrum technology) for reliable real time data communication, sufficient memory (128k to 256k in same embodiments) to store the care providers authorized functions, patient IDs and patient information, and a programmable, graphics liquid crystal display touch sensitive screen 22d (approximately $2 \times 4$ inches, in one embodiment, with back lighting) to facilitate data and keyboard display as required for data retrieval and input. A pocket terminal bar code reader 22c (non-contact point source optical device) to facilitate positive identification and ease of data entry, is integrated into the pocket terminal 22.

Figure 9:
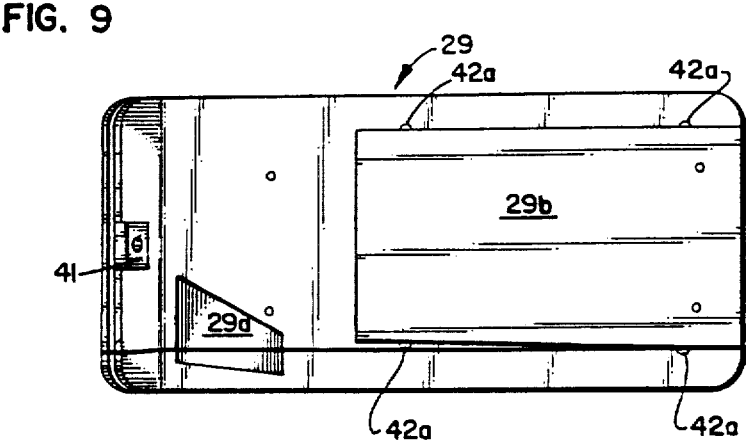
FIG. 9 is a rear elevational view of the portable handheld terminal keypad.

A detachable alphanumeric memory module keypad 29 may also be provided for use with the pocket terminal 22, wherein additional and dedicated function keys are provided, so as to allow an increase in customized specific instructions or notes to be input to the patient care system 20. The keypad 29 may be suitably attached to the touch screen 22d of the pocket terminal 22 such as by a cooperating ball 42a and detent 42b arrangement or other attachment method. In the embodiment shown in FIG. 9, a bottom side of the keypad 29 includes a recessed area 29a for positioning over the buttons 22b on the terminal and a projection 29b positioning in the recess of the LCD 22d. The keypad 29 shown interfaces with the pocket terminal 22 by use of an optical coupler; e.g., emitting optical signals from the keypad corresponding to user entries at the keypad 29 by use of an infrared emitter or other suitable optical emitter which is read by the bar code reader 22c or other suitable optical sensor in the pocket terminal 22 such as a light sensitive diode or the likes. Illustrated in FIG. 13 is a block diagram of a keypad 29 including user entry keys 70, control circuitry 72 for converting key entry signals into appropriate control signals for controlling the optical emitter 74. The keypad 29 includes a recess 41 in its housing which facilitates alignment of the emitter with the optical sensor of the pocket terminal 22. The keypad 29 is suitably connected to the pocket terminal 22 by an electrical connector, such as a three prong connector (not shown) so as to provide power, ground, and serial data between the two. The keyboard 29 shown utilizes a two line by twenty character liquid crystal display screen 43 for display of keyboard entries and functions.

The pocket terminal 22 facilitates data input via the touch screen keypad 22d while the terminal is resting in the hand or on a flat surface. This feature allows "one handed" operation of the terminal at the point of care. The liquid crystal display screen 22d facilitates selections via touch. Graphics displayed on the pocket terminal's liquid crystal display screen 22d may be used to facilitate data entry; for example, injection sites may be selected from a graphical representation of the body, and temperature may be selected from a graphical representation of a thermometer.

Figure 16:
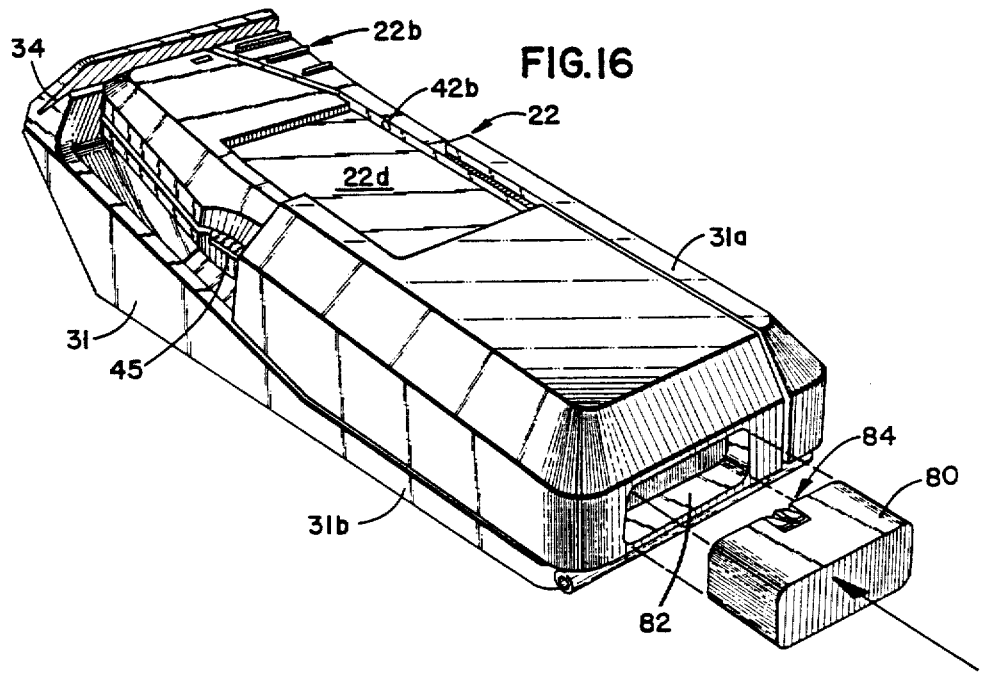
FIG. 16 is a perspective of an embodiment of a base unit capable of charging a replaceable battery pack.

The battery power of the pocket terminal 22 shall be sufficient to maintain continuous service for a minimum of eight to ten hours, and be largely recharged within a short time frame such as a thirty minute period. The pocket terminal 22 might include a rechargeable battery pack 80 which is removable for charging batteries at the base unit 31 as generally illustrated in FIG. 16 when extended use is required. In the embodiment of the base unit 31 shown, the battery pack 80 is inverted into an opening 82 of the base unit 31 such that electrical contacts 84 engage such controls (not shown) inside the opening 82 of the base unit 31 so as to be electrically interconnected to the recharging circuitry 52. A lithium battery back-up maintains the information stored in the pocket terminal's memory during the battery pack change period. A battery pack recharging unit is also available for use in storing and recharging spare battery packs. The base unit 31 might include a suitable electrical connector (not shown) to allow recharging of the spare battery packs upon electrical interconnection to the base unit 31.

Figure 8:
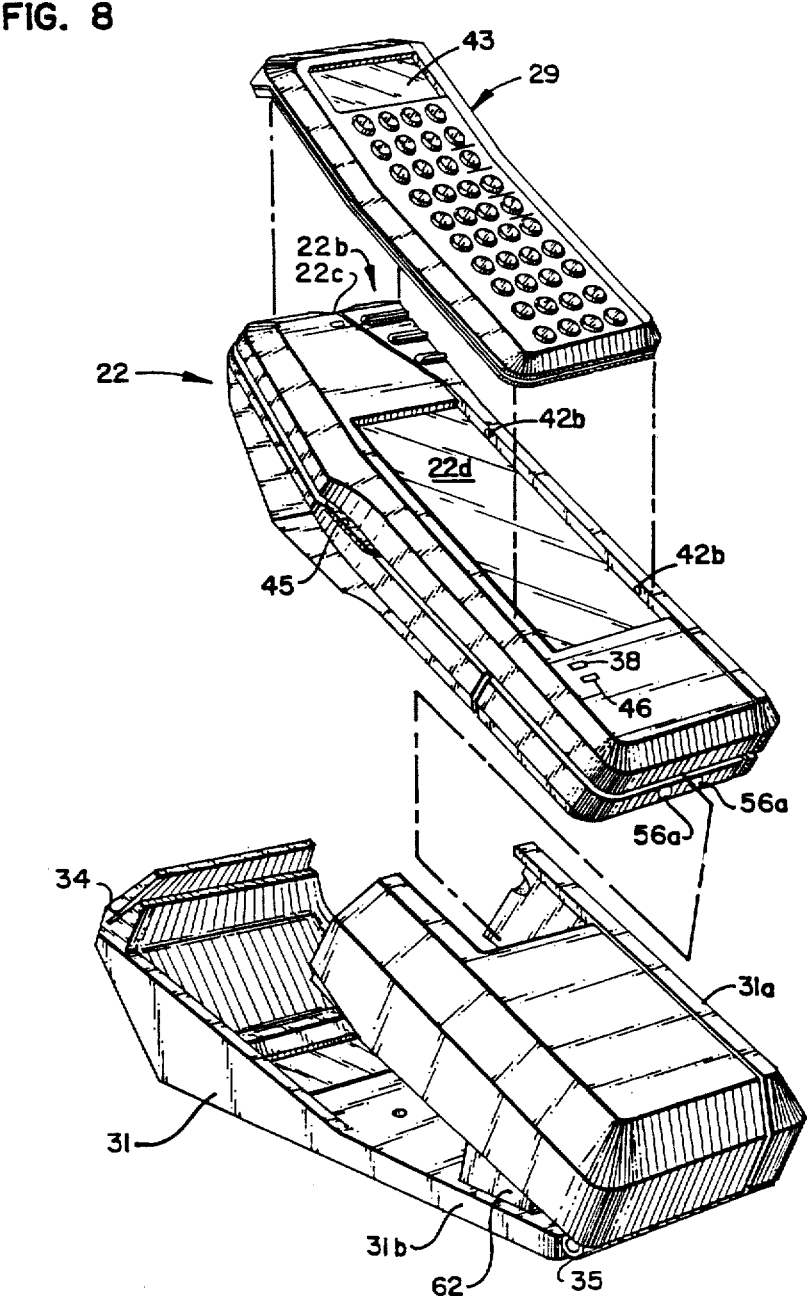
FIG. 8 is a exploded perspective view of the handheld terminal and holder, showing in addition an optional alphanumeric memory keypad.

The clinical display communication station 33 is typically located in patient rooms and wherever large amounts of data retrieval and/or inputs are required. The clinical display communication station 33 is suitably electrically connected to the base unit 31 and mounted therewith on a wall or other suitable location. The base unit 31 might obtain power from an AC outlet or from the clinical display communication station 33. As shown in FIG. 8, one embodiment of the clinical display communication station 33 includes a 640×400 cm back lit liquid crystal display monitor 39 and includes a data over voice modem 43 for communication with the applications processor 26 and radio frequency (RF) transceiver 37 for communication with the pocket terminal 22 and its associated logic/memory. As opposed to a DOV modem, the clinical display communication station 33 might include other communication devices and methods for communication with the nursing applications processor 26; e.g., a short haul modem, an RS-422 port, an RS-232 port, etc. The clinical display communication station 33 as shown is interconnected to a 28 volt DC or 15 volt DC central power supply 50 which can support multiple clinical display communication stations. The clinical display communication station 33 communicates directly with the pocket terminal 22 in the base unit 31 via the RF transceiver 37 for download and upload of data. In a preferred embodiment of the patient care system 20, a clinical display communication station 33 will be installed in the area of the nursing station 30, as well as in the patient rooms. This will facilitate pocket terminal 22 functions often performed at the nursing station 30 (e.g., controlled substance inventory) and can provide communication of additional charting entries at the nursing station 30 to avoid delays of data input at the nursing station personal computer 28.

Figure 11:
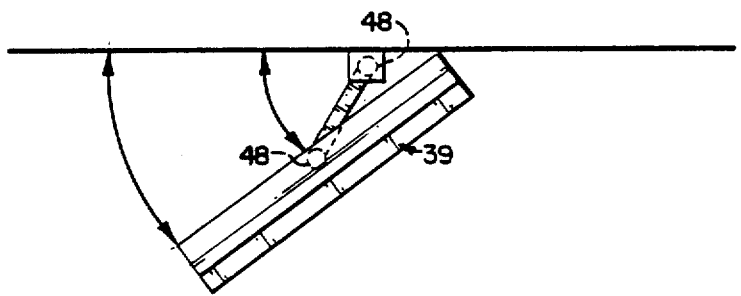
FIG. 11 is a top plan diagrammatic view of the hinge structure utilized in the liquid crystal display monitor, wherein the unit is partially extended away from a wall.
Figure 12:
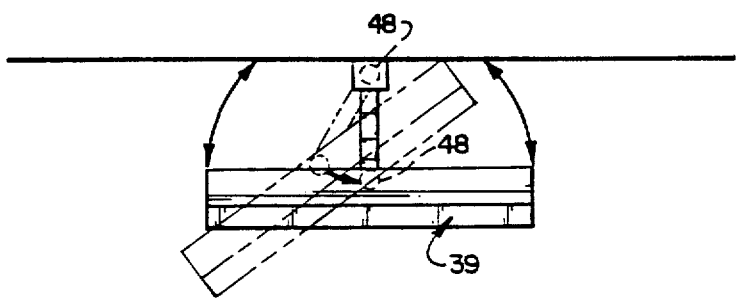
FIG. 12 is a top plan diagrammatic view of the liquid crystal display monitor of FIG. 11, in a fully extended position.

As shown in FIGS. 11 and 12, the liquid crystal display monitor 39 is provided with hinges 48 which allow the liquid crystal display monitor 39 to rotate in either a right or left direction. Further, the display screen may be moved within its housing in a vertical plane. Hinges 48 also allow the base station display monitor 39 to be pulled out from the wall before rotation occurs.

The "connection" or addressing to establish a communications link between the base station 32 and the pocket terminal 22 is accomplished by "reading" with the bar code reader 22c of the pocket terminal 22 a "location bar code" which defines a unique address of the base station 32. Thus the pocket terminal 22 is programmed with the same address as the base station 32. This must be done prior to activating a base station function or "sending" information from the pocket terminal 22 since the base station 32 will only communicate with a pocket terminal 22 having a matching address. Since the address of the pocket terminal 22 is programmable, the pocket terminal 22 can be programmed for use with any of the base stations 32 simply by scanning the location bar code associated with the base station 32 desired to be used. The location bar code would be mounted somewhere near or on the base station 32 and would be assigned as a part of the installation function. The base station 32 would each be assigned a unique address by downloading the address either from the file server 24 or the application processor 26. In an alternate embodiment, a cord would be used to attach the pocket terminal 22 to the base station 32 through the keyboard plug-in and the address assignment made. This process need only be done at installation and/or whenever the address needs to be changed.

The personal computer 28 at the nursing station 30 will also include a custom base station emulation 44 and bar code reader device and optionally either a data over voice modem or short haul modem. This personal computer 28 will support use access to either the hospital information system or patient care system 20. The nursing station personal computer 28 will communicate directly to an applications processor 26 which provides distributed processing for patient care system applications software modules. Each applications processor 26 will be linked via a local area network backbone to the central file server 24. An optional voice recognition module may be added to the nursing station personal computer 28 for enhanced data entry capabilities. This feature practically eliminates the typing associated with personalization or additions of textual information to the base station selected entries for care plans and patient assessment charting.

In use, a preferred embodiment of the current invention calls for the nurse, at the beginning of his/her shift, to sign onto the system at the base unit 31 located at the nursing station 30. The system checks his/her user ID and bar code against the user security file. If the sign-on data matches that in the use security file, the system checks the use assignment file and then uploads the appropriate pocket terminal pathways (based on the user security definition), and the patient data associated with the patients assigned to the user (based on the user type and assignment file definition). The user is now signed onto the system via his/her portable terminal 22 for the duration of his/her shift. The user now has access to his/her patients' latest vital signs, fluid balance entries, scheduled medications administered and medications given as necessary and all scheduled activities (including medications due, treatments due, interventions scheduled) for this shift, and all current "as necessary" types of orders.

Sample contents of the portable data base accessed through the pocket terminal 22 would include:
  assigned patients (up to 20 patients)
  latest information, i.e. vital signs, fluid balance totals so far today and thus far this shift, medications administered - scheduled (last scheduled doses administered) and as necessary (latest administered dose of each "as necessary" order within past 6 hours-time frame defined by hospital parameters) (estimated at 30 data elements per patient)
  all scheduled activities for this shift, for example, medications due, treatments due, interventions scheduled (estimated at 30 actions per patient)
  all current "as necessary" orders, e.g., medications, treatments or interventions (estimated at 10 per patient)

Contents of the data base are defined by hospital parameter table and may vary by patient type, e.g., inpatient ICU, OB, outpatient, or by type of user, e.g., RN, LPN, Nurse Assistant.

The nurse would carry the pocket terminal 22 with him/her as care is provided through the shift. The data uploaded to the pocket terminal 22 is available at all times to the nurse as he/she goes through the day and is automatically updated with each base station 32 or central data base interaction. The nurse may retrieve information from this portable data base at any time and in any location. This information will provide the nurse with a complete list of things to be done for his/her patients and a quick reference into recently provided care.

A sample of portable base retrieval functions includes:

Main Menu

Scheduled Actions (lists all scheduled actions in time sequence and then assorted in room/bed sequence)

By Patient (sorted in room/bed sequence and then in time sequence)

Data Review (touch this line to view first patient list and then categories of info)

Scratch Pad Worksheet

Medication Administration (must read patient bar code)

IV Administration (must read patient bar code)

Disposable Usages (must read patient or BC bar code)

Vital Signs Documentation (must read patient bar code)

Base Station Functions (must read patient bar code)

Data Review (first displays a list of assigned patients to select from, after patient selected shows options below)

Current Patient Data (sorted in data sequence as defined in parameter table)

Base Station Data Review

When the nurse enters the patient room and reads the patient bar code (the nurse need not read his/her bar code as the user ID is retained in the pocket terminal 22 from the original sign-on), the base station 32 automatically sends a request to the central fileserver 24 to update the nurse's portable data base with any new information entered since the last update (i.e., changed or new orders for any of his/her patients). The base station 32 may then be used in the normal manner for data retrieval or data input. Functions may also be performed with the pocket terminal 22 and sent via the clinical display communication station 33 or the nursing station 30 for validation and central data base update. Each time the pocket terminal 22 communicates with a base station 32, the portable data base for that nurse and all patients he/she is assigned to is updated with any new or changed data since the last communication (including new patient assignments). This ensures that the health care professional is always using valid, up-to-date information when providing care.

As scheduled actions (e.g., medications to be given or treatments to be carried out) become due (time frame defined by a customized hospital parameter table) a yellow reminder light 46, one of the status lights 22f on the pocket terminal 22 is turned on as a reminder to the nurse. (Optionally, an audible beep may also be sounded.) A message is also displayed on the pocket terminal liquid crystal display 40 informing the nurse of the item needing attention.

The nurse may retrieve information about his/her patients from the portable data base at any time. The data may be accessed by reading the patient's bar code identification or the nurse may request a list of his/her patients to be displayed on the pocket terminal 22 display, then select the patient and type of data he/she wants to review. This allows the nurse access to patient data even when away from the bedside and patient. To chart information about the patient or to update/status a scheduled order, the nurse must identify the patient via the usual bar code method.

A "scratch pad" capability is also available on the pocket terminal 22. This feature allows the nurse to make brief notes (e.g., check ice bag) or "mark" or highlight certain orders as reminders. This scratch pad data is retained in the pocket terminal 22 only and is not sent for update to the central data base. Many of these notes are menu or special function selections from the terminal's liquid crystal display screen 40.

A sample scratch pad work sheet might include the following:

---
Rm #
____ ck ice bag
____ provide fluids
____ call DR
____ ck dressings
____ pain med
____ -
---

A similar function to the nurse call/beeper is an order alert initiated by the applications processor 26. This feature would page a nurse's pocket terminal 22 whenever any of his/her patients had new orders. The alert light 46 would flash to notify the nurse and would remain on until the nurse acknowledged the message on the touch screen 40. An audible beep in addition to the flashing light 46 may optionally be provided. A message on the pocket terminal screen 40 would indicate which patient had new orders. The nurse could then be sure to initiate central data base communication to update his/her portable data base with the new data.

At the end of the shift the nurse would set the pocket terminal 22 into the base unit 31 and thus sign off the system. The pocket terminal 22 would then be available for use by another person.

In the preferred embodiment of the current invention, any patient's data may be accessed by any authorized user, even if that user was not assigned to the patient, simply by reading the patient's ID band. This would facilitate care of the patient by another professional when that patient's nurse/doctor is unavailable.

The above-described capabilities would be available not only for nursing, but also for other care providers within the hospital (e.g., respiratory therapists, physical therapists, dieticians, laboratory technicians, social workers) and to physicians. The physician may have a pocket terminal 22 and base unit 31 in his/her office, sign in prior to making hospital rounds or going elsewhere, and have available valuable information about the patients no matter where the physician was physically located. The pager capability described above would only be available within the hospital and not in the community at large.

The pocket terminal 22 and the base unit 31 can be used at a remote site, not interconnected to the patient care system 20. For example, the base unit can be sued to download patient data from a memory module; e.g., memory and supporting electronics, on a card similar to the card 25 into random access memory of the pocket terminal 22. The date might include the list of medications and/or procedures to be administered to that particular patient. As the health care professional administers the medications, etc., to the patient, they will be verified against the downloaded data. As the health care professional administers to the patient, the health care professional's actions will be verified against the down loaded data. Once the health care professional is through administering care to the patient, the updated health care data in the pocket terminal 22 might be uploaded into the memory module on the card 25. The pocket terminal 22 might also be taken back to the patient care system 20 and the information in the memory of the pocket terminal 22 downloaded into the patient care system 20. It will be appreciated that in this embodiment, the pocket terminal 22 need not have an RF transceiver (modem) since the RF terminal most likely would not be used in the patient's home. Because of these and other features, the pocket terminal 22 and base station 32 have particular utility for administering health care at individuals' homes. In one application, the patient might be given a memory module; e.g., a card including a ROM and supporting circuitry, when they leave the clinic or the hospital which would include the patient orders, vital signs, etc.

In yet another embodiment of the pocket terminal, a portable/removable modem might be used with the pocket terminal 22 such that when a health care professional is in the patient's home, the health care professional can download the patient data to the hospital system by use of the telephone at the patient's home or other convenient location. In addition, the modem could also be used to upload information from the hospital computer system to the memory of the pocket terminal 22.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A portable handheld terminal, comprising:
   (a) a housing;
   (b) programmable touch sensitive display means disposed on the housing for display of information and for entry of information whereby the response of the display means to the touch can be varied;
   (c) optical sensing means disposed in the housing for sensing optically transmitted information and including bar code reader means for reading bar code indicia on an object;
   (d) electromagnetic transceiver means disposed within the housing for transmitting and receiving electromagnetic signals;
   (e) detachable keyboard means detachably mounted on the housing for entry of information, the detachable keyboard means including a display for display of information, the detachable keyboard being mounted over touch sensitive the display means, the keyboard means including optical transmitter means for optically transmitting user entered information to the optical sensing means of the portable handheld terminal;
   (f) microcomputer control means including microprocessor and associated memory contained in the housing and operatively interconnected to the detachable keyboard means; display means, optical sensor means, and electromagnetic transceiver means for controlling operation of the portable handheld terminal; and
   (g) power supply means for powering the portable handheld terminal.

2. An apparatus in accordance with claim 1, wherein the housing has a substantially flat back surface, providing for placement of the portable handheld terminal on a flat surface, thereby allowing one hand usage.

3. An apparatus in accordance with claim 1, wherein the power supply means comprises a rechargeable battery pack.

4. An apparatus in accordance with claim 3, wherein the battery pack is replaceable, the portable handheld terminal including a backup power supply to maintain information stored in memory upon removal of the battery pack.

5. An apparatus in accordance with claim 3, further including backup power supply means for maintaining information stored in the memory of the portable handheld terminal.

6. An apparatus in accordance with claim 1, wherein the portable handheld terminal includes operational on/off switch disposed on a side wall surface of the housing.

7. An apparatus in accordance with claim 1, wherein the optical sensing means comprises a non-contact point source optical device, whereby the optical sensing means is self-scanning.

8. An apparatus in accordance with claim 1, wherein the touch sensitive display means provides for graphic display of alphanumeric information.

9. An apparatus in accordance with claim 1, further comprising security means for verifying user entered user identification wherein the user must enter his/her user identifier number to gain access to information stored in the memory of the portable handheld terminal.

10. An apparatus in accordance with claim 1, wherein the housing includes a recessed opening proximate the sensing means.

11. An apparatus in accordance with claim 1, wherein the portable handheld terminal comprises ready indication means for signaling readiness for use.

12. An apparatus in accordance with claim 1, wherein the portable handheld terminal further includes status means for indicating selected operational status of the portable handheld terminal.

13. An apparatus in accordance with claim 1, wherein the status means comprises a warning indicator indicating an improper operational condition.

* * * * *